United States Patent [19]

Watts

[11] 4,115,410

[45] Sep. 19, 1978

[54] PROCESS FOR MAKING PEROXYCARBOXYLIC ACID

[75] Inventor: Herbert L. Watts, Brandenburg, Ky.

[73] Assignee: Olin Corporation, New Haven, Conn.

[21] Appl. No.: 833,417

[22] Filed: Sep. 15, 1977

[51] Int. Cl.² ............... C07D 301/14; C07C 179/12
[52] U.S. Cl. ........................... 260/348.25; 260/502 R
[58] Field of Search ....................... 260/502 R, 348.25

[56] References Cited

U.S. PATENT DOCUMENTS

| | | | |
|---|---|---|---|
| 2,861,100 | 11/1958 | Humber | 260/502 R |
| 3,019,234 | 1/1962 | Korach | 260/348.5 L |

FOREIGN PATENT DOCUMENTS 2,141,155  3/1973  Fed. Rep. of Germany ...... 260/502 R

*Primary Examiner*—Norma S. Milestone
*Attorney, Agent, or Firm*—Robert J. Feltovic; Thomas P. O'Day

[57] ABSTRACT

A method of making a peroxycarboxylic acid is described in which hydrogen peroxide is reacted with carboxylic acid in the presence of a catalyst acid to produce a reaction mixture containing peroxycarboxylic acid, unreacted carboxylic acid and the catalyst acid. This reaction mixture then is treated with ammonia to neutralize the catalyst acid, and the ammonium salt formed is removed in an aqueous phase. The mineral acid-free peroxycarboxylic acid reaction mixture may then advantageously be utilized as an oxidant. The peroxy-acids readily add oxygen to unsaturated compounds to produce epoxide compounds.

18 Claims, No Drawings

PROCESS FOR MAKING PEROXYCARBOXYLIC ACID

Various methods have previously been proposed for the preparation of peroxyacids. Peroxyacids (peracids) are acyl hydroperoxides and are most commonly produced by the acid-catalyzed esterification of hydrogen peroxide. Early peroxycarboxylic acid indirect oxidation techniques recognized the use of a catalyst acid, e.g., a mineral acid, such as sulfuric acid, to promote the reaction of hydrogen peroxide with carboxylic acid to obtain a peroxycarboxylic acid-containing mixture. The peroxycarboxylic acid reaction mixture is useful as an oxidant. Typically, peracids are known to readily add oxygen to unsaturated compounds to form three-membered oxirane ring compounds, generally known as epoxides. For example, epoxidation of highly unsaturated oils with peroxyacids results in products useful as plasticizers for vinyl resins and in the formulation of epoxy resins.

In a particular utility, the preparation of alkylene oxides, one method often suggested in the literature is the indirect oxidation of alkylenes via peroxycarboxylic acid techniques. However, relatively low alkylene oxide yields and the production of undesirable amounts of various by-products during epoxidation rendered these peroxyacid route techniques economically uncompetitive. In time, it was appreciated that the actual indirect oxidation reaction mixture should be substantially free of the acid catalysts from the peroxyacid-forming reaction. These catalyst contaminants serve to catalyze esterification and hydrolysis side reactions during desired epoxidation (see U.S. Pat. No. 3,341,556). One of the developments which the prior art literature describes in the preparation of peroxycarboxylic acid is the use of various ion exchange resins as peroxycarboxylic acid production catalysts in place of mineral acid catalysts. The use of these resins sometimes enhances peroxycarboxylic acid production and, in turn, minor increases in subsequent epoxidation yields are sometimes observed. Thus, U.S. Pat. Nos. 3,140,312; 3,330,207; 2,976,265; and 2,910,504, for example, all suggest the use of various ion exchange resin catalysts in the production of peroxycarboxylic acids by the reaction of hydrogen peroxide with carboxylic acid. These ion exchange resins are commercially available products which have functional acidic groups, such as sulfonic, carboxylic, phosphoric and phosphorous groups and combinations of these, directly attached to the carbon structure resins, e.g., styrene divinyl benzene-based structures.

Although minor increases in peroxyacid and epoxide, such as alkylene oxide, yields are sometimes achieved in substituting ion exchange resins for catalyst acids in the peroxyacid reaction, the use of these resins creates its own problems. For example, because the acidic ion exchange resin is being depleted of its acid sites as it is being used in the reaction of hydrogen peroxide and carboxylic acid to produce peroxyacid, the amount of catalysis may decrease as a function of time and eventually may lead to undesirable levels of productivity and/or yield. Thus, the ion exchange resins may have to be reactivated periodically and this means shut-downs or by-passing with auxiliary equipment. Either corrective approach is very expensive on a commercial scale.

Now, it has been discovered that mineral acid-free yields of peroxycarboxylic acid can be achieved through use of an improved method including an acid catalyzed peroxycarboxylic acid-forming step, after which the acid catalyst is neutralized by reaction with ammonia to form an ammonium salt which is then extracted prior to subsequent use of the peracid as an oxidant, such as in an epoxidation reaction involving the peroxycarboxylic acid and an alkylene oxide.

The peroxycarboxylic acid-forming reaction generally can be characterized as an acid catalyzed esterification of hydrogen peroxide. A peroxyacid is formed when a carboxylic acid is mixed with hydrogen peroxide in the presence of an acid catalyst, typically a mineral acid, such as sulfuric acid, as follows:

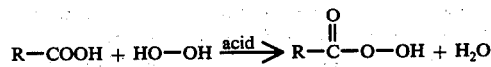

wherein R is hydrogen, a substituted or unsubstituted alkyl having 1 to 4 carbon atoms or a substituted or unsubstituted aryl having up to 10 carbon atoms. Preferably, R is hydrogen, an unsubstituted alkyl having 1 to 2 carbon atoms or an unsubstituted aryl having up to 7 carbon atoms. Among the most useful carboxylic acids are those in which R is hydrogen, methyl, ethyl or phenyl. Thus, the carboxylic acid starting material may be a relatively lower molecular weight acid, such as acetic acid, propionic acid, and the like, or it may be a higher acid such as phthalic acid. Acetic acid is most preferred.

The hydrogen peroxide reacted with the carboxylic acid in the peroxyacid production is preferably dissolved in a solvent which is inert to all of the principal materials used in making the peroxyacid and the alkylene oxide. Among these solvents are those represented by the formula R'COOR" in which R' and R" are each independently selected from substituted and unsubstituted alkyls having 1 to 5 carbon atoms. Preferred solvents are esters of the above formula in which R' is methyl and R" is ethyl, n-butyl, n-propyl, isopropyl, sec-butyl, t-butyl or n-pentyl and those esters in which R' is ethyl and R" is ethyl, n-propyl or isopropyl. A most advantageous solvent for the hydrogen peroxide is isopropyl acetate or n-butyl acetate.

In the preferred reaction scheme, a carboxylic acid of the formula RCOOCH, wherein R is defined above, is combined with hydrogen peroxide, in a proportion generally of about 1.0 mole to about 3.0 moles of carboxylic acid, preferably about 1.3 to about 2.0 moles of carboxylic acid, and most preferably about 1.5 to 1.7 moles of carboxylic acid, per mole of hydrogen peroxide. The hydrogen peroxide may, as mentioned, preferably be in a solvent solution which may contain about 2 to about 20% of hydrogen peroxide, preferably about 10 to about 15%, based on the weight of the solution.

The hydrogen peroxide and carboxylic acid are reacted in a reactor which is inert to the reactants and products involved, including the catalyst acid. The hydrogen peroxide may be fed to the reactor in a separate stream or may be combined with the carboxylic acid just prior to being fed to the reactor. The catalyst acid may likewise be fed to the reactor by itself or may be combined with one or more of the reactants prior to being fed to the reactor. A preferred technique involves combining the catalyst acid with the carboxylic acid outside the reactor and then combining this mixture with the hydrogen peroxide to form a single reactant stream which is fed to the reactor.

The catalyist acid employed in the method of the present invention is any acid which may be used to promote the formation of the peroxyacid. Among these catalyst acids are organic acids, such as toluene sulfonic acid, and methane sulfonic acid, or mineral acids, such as phosphoric acid and sulfuric acid. The amount of catalyst acid employed is the conventional amount used to produce the peroxyacid. For purposes of illustration, generally about 0.1 to about 2.0, and preferably about 0.2 to about 0.5% sulfuric acid typically is used to form the peroxyacid, based on the weight of the carboxylic acid feed, although more acid may be employed with significantly detrimental effects. This amount of sulfuric acid is based on dry weight although aqueous sulfuric acid may be used. The specific amount of catalyst acid used, of course, depends upon the particular acid chosen. For example, if phosphoric acid is used instead of sulfuric acid, about 5 to about 20% by weight is generally used. The peroxyacid reactants are maintained in the peroxyacid reactor in the presence of the catalyst acid until a desirable amount of peroxyacid is produced. Generally, the peroxyacid reactor is maintained at a temperature of about 40° C. to about 65°C., preferably about 50° C. to about 60°C. The reactor is evacuated to a pressure of about 0.10 to about 0.7 atmospheres, preferably about 0.2 to about 0.5 atmospheres, most preferably about 0.2 to about 0.3 atmospheres. Reduced pressures are generally preferred and may vary depending upon the choice of solvent used.

When the hydrogen peroxide reacts with carboxylic acid, a reaction mixture is produced which contains water, peroxycarboxylic acid, unreacted carboxylic acid and catalyst acid, as well as the hydrogen peroxide solvent, if used. Since water is a product of the reaction above, its removal from the reaction mixture will enhance the formation of the peroxyacid. For this reason, the peroxyacid reactor is maintained at pressure and temperature levels so as to distill off substantially all of the water by-product at it is produced. If an ester solvent is also present, some of it may also evaporate off in the form of an azeotrope with the water. At any rate, the reactor is maintained under temperature and pressure conditions as described above so as to assure the removal of substantially all of the water from the reactor to produce a reaction mixture containing peroxycarboxylic acid and catalyst acid.

The reaction mixture containing the peroxycarboxylic acid, carboxylic acid and catalyst acid generally contains about 5 to about 40%, preferably about 20 to about 30%, peroxycarboxylic acid; about 2 to about 50%, preferably about 8 to about 20%, carboxylic acid; and about 0.1 to about 5.0%, preferably about 0.2 to about 1.0%, catalyst acid, e.g., when sulfuric acid is used. These percentages are based on the solvent-free weight of the reaction mixture removed from the peroxacid reactor. When phosphoric acid or methane or toluene sulfonic acid is used, a proportionate amount of catalyst acid to the amount fed into the peroxyacid reactor is obtained. If solvent is present in the reaction mixture, generally about 10 to about 95%, e.g., about 25 to about 55% solvent may be present based on the total weight of the reaction mixture, although the amount will vary depending upon the particular solvent chosen.

The peroxycarboxylic acid reaction mixture, containing carboxylic acid and catalyst acid, has been used, as is, to convert an alkylene compound to its corresponding alkylene oxide. It is known that peroxyacids readily add oxygen to these unsaturated compounds to produce alkylene oxides with a three-membered oxirane ring, commonly known as epoxides. However, presence of the acid catalyst from the peroxycarboxylic acid reaction mixture serves to catalyze side reactions during epoxidation. By serving to catalyze esterification and hydrolysis side reactions, presence of these acid catalysts significantly reduce the yield of the desired alkylene oxide products.

Therefore, according to the present invention, the peroxycarboxylic reaction mixture first is treated to remove the acid catalyst prior to the subsequent reaction of the peroxycarboxylic acid as an oxidant. In order to effectively remove the acid catalyst, the peroxycarboxylic reaction mixture is treated with ammonia, in vapor phase or anhydrous form, to neutralize the acid. Gaseous ammonia is preferred, because of its ease of handling.

The ammonia is added in an amount sufficient to neutralize the catalyst acid in the reaction mixture obtained from the peroxyacid reactor. For example, when sulfuric acid is the catalyst acid, about 1.8 to about 4.0 moles and preferably about 2.0 to about 2.2 moles of ammonia per mole of catalyst acid should be used.

Neutralization of the acid with the ammonia base results in the formation of an ammonium salt which precipitates from the organic reaction mixture. For example, when a sulfuric acid catalyst is used, an insoluble ammonium sulfate precipitate forms from the reaction with the ammonia.

Use of ammonia to neutralize the catalyst acid according to the present invention results in increased alkylene oxide yield in subsequent epoxidation reactions involving the peroxycarboxylic acid reaction mixture. Use of other neutralizing bases has been found to involve handling problems or undesirable decomposition of the peroxyacid. For example, use of a base, such as sodium hydroxide, a water-producing base, has been found to initiate hydrolysis of the peroxyacid to the carboxylic acid and hydroperoxide. Use of any strong base dictates the exercise of caution, since the peroxyacid exhibits unstability at pH levels of about 6 or higher. Bases selected from ammonium, alkali metal, and alkali earth metal acetates and propionates have been found to be useful neutralization agents, but these salts are inconvenient to physically handle and transfer and, thus, introduce processing problems on a commercial scale. On the other hand, neutralization with ammonia, according to the present invention, creates no transfer problems and, for example, can readily be introduced into a reaction mixture merely by bubbling the gas through a neutralization reactor.

Once the acid catalyst, e.g., sulfuric acid, has been completely neutralized by the ammonia, the resulting ammonium salt, e.g., ammonium sulfate, should be removed in order to avoid mechanical difficulties in ensuing reactions wherein the peroxycarboxylic acid is used. As described above, the ammonium salt is insoluble in the organic reaction mixture and accordingly forms as a precipitate in the peroxyacid reaction mixture. Removing the precipitate can be achieved by common means, such as filtering or decanting. However, such standard methods may sometimes by unsatisfactory, as they may result in product loss through incomplete separation and/or add time-consuming, cost-increasing steps which complicate the overall process.

Therefore, in accordance with the preferred embodiments of the present invention, the ammonium salt precipitate can conveniently be removed by allowing it to settle from the organic peroxycarboxylic acid reaction mixture into an underlying aqueous phase in which the salt readily dissolves. This removal procedure is complicated, however, since water, as noted above, cannot be allowed to come in contact with the reaction mixture itself. Water causes the equilibrium of the peroxycarboxylic acid reaction mixture to shift and revert back to favor the carboxylic acid and hydroperoxide. In order to resolve this critical problem, the present invention introduces an interface barrier layer to separate the organic peroxycarboxylic reaction mixture from the underlying aqueous layer. Accordingly, the ammonium salt precipitate is allowed to pass from the peroxyacid reaction mixture, through the barrier layer, to the underlying aqueous layer where it dissolves for ready removal. The interface barrier layer may be any organic solvent which is inert to the components of the peroxyacid reaction mixture, immiscible with water, and a non-solvent for the ammonium salt. Among useful solvents are the same solvents that are described above for use in dissolving the hydrogen peroxide for introduction into the peroxyacid-forming reaction. It is most advantageous to use the same solvent as an interface barrier that was used as the hydrogen peroxide solvent. Isopropyl acetate or n-butyl acetate is particularly preferred.

After ammonium salt has settled from the peroxyacid reaction mixture, this top organic layer can be drawn off with no loss of product and with the introduction of a minor amount of additional interface solvent. This peroxycarboxylic acid reaction mixture now advantageously can be used for alkylene oxide production.

The peroxycarboxylic acid reaction mixture produced according to the present invention is particularly suited for use in the indirect oxidation of alkylenes. The alkylene oxides produced by the method of the present invention are those derived from unsubstituted, monoolefinically bonded, lower alkylenes having 2 to about 15 carbon atoms, including mixtures of these alkylenes. Among the preferred unsubstituted, mono-olefinically bonded, lower alkylenes of the present invention are those having 3 to 6 carbon atoms. Propylene is particularly preferred.

The unsubstituted, mono-olefinically bonded, lower alkylene is combined with the reaction mixture containing peroxycarboxylic acid and carboxylic acid after the catalyst acid therein has been neutralized and the ammonium precipitate removed. These reactants are combined inside an epoxidation reactor or just prior to being fed to an epoxidation reactor. The reaction mixture and the alkylene are proportioned so as to employ at least a stoichiometric amount or an excess of alkylene as compared to the peroxycarboxylic acid. Generally, about 1.0 mole to about 4.0 moles, and preferably about 1.5 to about 2.0 moles of alkylene are used per mole of peroxycarboxylic acid in the reaction mixture. The preferred method of epoxidation is to contact the unsubstituted, mono-olefinically bonded, lower alkylene with the peroxycarboxylic acid-containing reaction mixture under conditions which maintain the alkylene in the liquid phase, although gaseous alkylene, e.g., propylene, may be employed.

The epoxidation reaction is carried out at temperatures generally ranging from about 37° C. to about 100° C., preferably about 48° C. to about 60° C., although the specific temperatures chosen will depend upon the particular alkylene or mixture of alkylenes, being epoxidized. Pressures will also vary depending upon the reactants, but generally a pressure of about 2.5 to about 30 atmospheres, e.g., about 5 to about 15 atmospheres, may be used. It should be noted that, in any case, epoxidation temperature and pressure conditions should be chosen so as to enhance the epoxidation reaction without being so extreme as to cause explosion or carboxylic acid decomposition.

The alkylene oxide obtained by the epoxidation reaction is readily produced without the need for an epoxidation catalyst. The alkylene oxide is withdrawn from the epoxidation reactor in a mixture containing unreacted alkylene, carboxyic acid and minor amounts of by-products. Any of the conventional recovery techniques may be employed to isolate the alkylene oxide, as are well known in the art. Methods such as are described in U.S. Pat. Nos. 3,654,094 and 3,580,819 may be employed. For example, a series of distillations may be used to isolate each of the components in the mixture withdrawn from the epoxidation reactor and the unreacted alkylene and carboxylic acid may be recycled and used as feed in the overall process. The degree of purification of the alkylene oxide obtained ultimately depends upon the subsequent use of the product and is a matter of choice.

Reference is now made to the following examples which show preferred embodiments of the present invention, but do not limit the scope of the invention thereto. All parts and percentages are by weight unless otherwise specified.

COMPARATIVE EXAMPLE A

To establish the improved results using peroxycarboxylic acid prepared by the method of the present invention over such peroxyacid prepared by prior art methods, the following run is made which represents the prior art in which peracetic acid, including sulfuric acid as the catalyst acid, is used as an oxidant in the preparation of propylene oxide.

One hundred grams of a solution of peracetic acid in isopropyl acetate containing 11.45% peracetic acid, 6% acetic acid, 0.75% sulfuric acid, by weight, remainder being isopropyl acetate, is charged to a pressure reactor. Next, 28.1 grams of propylene, containing about 10% by weight of propane, is fed to the reactor in the liquid phase at a pressure of about 11 atmospheres for about two hours, after which the excess propylene is vented. A product mixture is obtained weighing 99.8 grams containing 5.0-5.05% by weight of propylene oxide. The yield of propylene oxide is determined to be about 57.2%.

EXAMPLE I

A peracetic acid reaction mixture containing 22.4% by weight peracetic acid, 26.5% by weight acetic acid, 0.75% by weight sulfuric acid, and the balance isopropyl acetate was prepared by reacting hydrogen peroxide, in isopropyl acetate solution, with acetic acid, using sulfuric acid as a catalyst, in a preacid reaction vessel.

In order to neutralize the sulfuric acid catalyst in the mixture, 0.39%, by weight, a slight stoichiometric excess, of gaseous ammonia was introduced into the reaction mixture. This $H_2SO_4$-neutralized peracetic acid solution was then pumped into a decant device and successive portions first of isopropyl acetate and then of water were forced into the base of the decant device. The decant device was arranged so that the interface between the organic barrier layer (isorpopyl acetate) and the water could be visibly observed. As the precipitated ammonium sulfate from the ammonia neutralization of the sulfuric acid catalyst in the peracetic acid mixture was allowed to settle from the reaction mixture, it was observed to pass through the isopropyl acetate barrier layer into the underlying aqueous layer where it dissolved and went into solution. The top organic reaction mixture, free of precipitated solids and much more easily handled, was decanted off.

The peracetic acid mixture was then fed into a pressure reactor, at 240 psig and 154°-157° F., at the rate of 20.36 lbs/hr. Propylene, at 90% purity (balance propane), was also introduced continuously at the rate of 5.89 lbs/hr. At these feed rates, the average residence time in the reactor was 94 minutes.

The reaction product effluent from the reactor was analyzed to contain 2.0% peracetic acid and 10.8% propylene oxide. This indicates a yield of propylene oxide of about 92.9%.

What is claimed is:

1. In a method of preparing a peroxycarboxylic acid-containing reaction mixture comprising reacting a carboxylic acid with hydrogen peroxide in the presence of an acid catalyst, the improvement characterized by:

eliminating the acid catalyst present in the peroxycarboxylic acid reaction mixture by adding ammonia to said reaction mixture in an amount sufficient to neutralize said catalyst and form an insoluble precipitate in the reaction mixture, and removing said precipitate from the reaction mixture prior to subsequent use of the peroxycarboxylic acid as an oxidant by introducing an underlying aqueous phase beneath said reaction mixture subsequent to introduction of an interface organic solvent barrier layer effective to separate said reaction mixture from said aqueous phase and allowing said precipitate to settle from said reaction mixture through the interface organic solvent barrier layer into the aqueous layer.

2. The method of claim 1 wherein the ammonia is in the form of gaseous ammonia.

3. The method of claim 2 wherein the acid catalyst is selected from sulfuric acid, phosphoric acid, toluene sulfonic acid and methane sulfonic acid.

4. The method of claim 3 wherein the acid catalyst is sulfuric acid.

5. The method of claim 4 wherein about 1.8 to about 4.0 moles of ammonia are used per mole of acid catalyst.

6. The method of claim 5 wherein about 2.0 to about 2.2 moles of ammonia are used per mole of acid catalyst.

7. The method of claim 1 wherein said carboxylic acid is represented by the formula R—COOH, wherein R is hydrogen, a substituted or unsubstituted alkyl having 1 to 4 carbon atoms or a substituted or unsubstituted aryl having up to 10 carbon atoms.

8. The method of claim 7 wherein said carboxylic acid is represented by the formula R—COOH, wherein R is hydrogen, methyl, ethyl or phenyl.

9. The method of claim 8 wherein said carboxylic acid is acetic acid.

10. The method of claim 1 wherein said interface organic solvent barrier layer is a compound represented by the formula R'COOR", wherein R' and R" are independently selected from substituted and unsubstituted alkyls having 1 to 5 carbon atoms.

11. The method of claim 10 wherein said interface organic solvent barrier layer is a compound represented by the formula R'COOR", wherein R' is methyl and R" is selected from ethyl, n-butyl, n-propyl, isopropyl, sec-butyl, t-butyl and n-pentyl.

12. The method of claim 10 wherein said interface organic solvent barrier layer is a compound represented by the formula R'COOR", wherein R' is ethyl and R" is selected from ethyl, n-butyl, n-propyl and isopropyl.

13. The method of claim 10 wherein said interface organic solvent barrier layer is isopropyl acetate.

14. The method of claim 10 wherein said interface organic solvent barrier layer is n-butyl acetate.

15. The method of claim 1 wherein said insoluble precipitate is ammonium sulfate.

16. In a method of preparing an alkylene oxide using a peroxycarboxylic method of indirect oxidation of an alkylene compound comprising reacting a carboxylic acid with hydrogen peroxide in the presence of an acid catalyst to produce a peroxycarboxylic acid reaction mixture and subsequently reacting this reactiion mixture with an unsubstituted, mono-olefinically bonded, lower alkylene to produce an alkylene oxide, the improvement characterized by:

eliminating the acid catalyst present in the peroxycarboxylic acid reaction mixture according to claim 1 by adding ammonia to said reaction mixture in an amount sufficient to neutralize said catalyst and form an insoluble precipitate in the reaction mixture, and removing said precipitate from the reaction mixture, prior to reacting said reaction mixture with the lower alkylene to produce the corresponding alkylene oxide.

17. The method of claim 16 wherein said alkylene compound is a lower alkylene having 3 to 6 carbon atoms.

18. The method of claim 17 wherein said lower alkylene is propylene.

* * * * *